United States Patent [19]

Moermann et al.

[11] Patent Number: 4,575,805
[45] Date of Patent: Mar. 11, 1986

[54] METHOD AND APPARATUS FOR THE FABRICATION OF CUSTOM-SHAPED IMPLANTS

[76] Inventors: Werner H. Moermann, Hofstrasse 104, CH-8044 Zuerich; Marco Brandestini, Gartenstrasse 10, CH-8702 Zollikon, both of Switzerland

[21] Appl. No.: 643,755

[22] Filed: Aug. 23, 1984

Related U.S. Application Data

[63] Continuation-in-part of Ser. No. 334,207, Dec. 24, 1981, abandoned.

[30] Foreign Application Priority Data

Dec. 24, 1980 [CH] Switzerland .................. 9561/80

[51] Int. Cl.[4] .................. G06F 15/46; G01B 11/24
[52] U.S. Cl. .................. 364/474; 364/168; 364/475; 356/2; 356/376; 33/511; 128/776; 250/237 G; 433/55; 433/68; 433/204; 433/223; 382/59
[58] Field of Search .................. 364/168, 474, 475, 414; 356/355, 356, 357, 358, 374, 376, 378, 2; 250/237 G; 382/59, 65, 68; 33/174 D; 128/776; 433/55, 68, 73, 204, 213, 214, 223

[56] References Cited

U.S. PATENT DOCUMENTS

| | | | |
|---|---|---|---|
| 3,614,237 | 10/1971 | Kyle et al. | 356/2 |
| 3,809,868 | 5/1974 | Villalobos et al. | 364/168 |
| 3,814,521 | 6/1974 | Free | 356/391 |
| 4,051,483 | 9/1977 | Suzuki | 356/376 |
| 4,084,244 | 4/1978 | Flötes | 364/474 |
| 4,102,578 | 7/1978 | Suzuki et al. | 356/374 |
| 4,146,924 | 3/1979 | Birk et al. | 364/513 |
| 4,158,507 | 6/1979 | Himmel | 356/376 |
| 4,182,312 | 1/1980 | Mushabac | 433/214 |
| 4,185,918 | 1/1980 | DiMatteo et al. | 356/2 |
| 4,202,630 | 5/1980 | Suzuki et al. | 356/374 |
| 4,212,031 | 7/1980 | Schmitt et al. | 364/474 |
| 4,234,306 | 11/1980 | Hamada et al. | 433/55 |
| 4,299,491 | 11/1981 | Waters et al. | 356/376 |
| 4,310,228 | 1/1982 | Terada | 128/6 |
| 4,353,693 | 10/1982 | Dérg et al. | 128/776 |
| 4,355,301 | 10/1982 | Issihiki et al. | 382/59 |
| 4,385,360 | 5/1983 | Yamada et al. | 364/475 |
| 4,480,636 | 11/1984 | Karaki et al. | 128/6 |
| 4,491,865 | 1/1985 | Danna et al. | 128/4 |
| 4,493,968 | 1/1985 | Brown | 356/376 |

FOREIGN PATENT DOCUMENTS

| 2936847 | 3/1981 | Fed. Rep. of Germany | 433/233 |
|---|---|---|---|
| 3003435 | 8/1981 | Fed. Rep. of Germany | 433/233 |

*Primary Examiner*—Jerry Smith
*Assistant Examiner*—John R. Lastova
*Attorney, Agent, or Firm*—Flynn, Thiel, Boutell & Tanis

[57] ABSTRACT

The surface characteristics of an organ that needs restoration, for example, a tooth which has been prepared for an inlay insertion, are read by means of a noncontact scan-head. The three-dimensional shape parameters of the implant required to restore the tooth in function and appearance are computed on the basis of the recorded contour data. These parameters are then used in a program sequence which controls a milling, cutting or erosive process in order to manufacture the restorative inlay while the patient waits.

21 Claims, 12 Drawing Figures

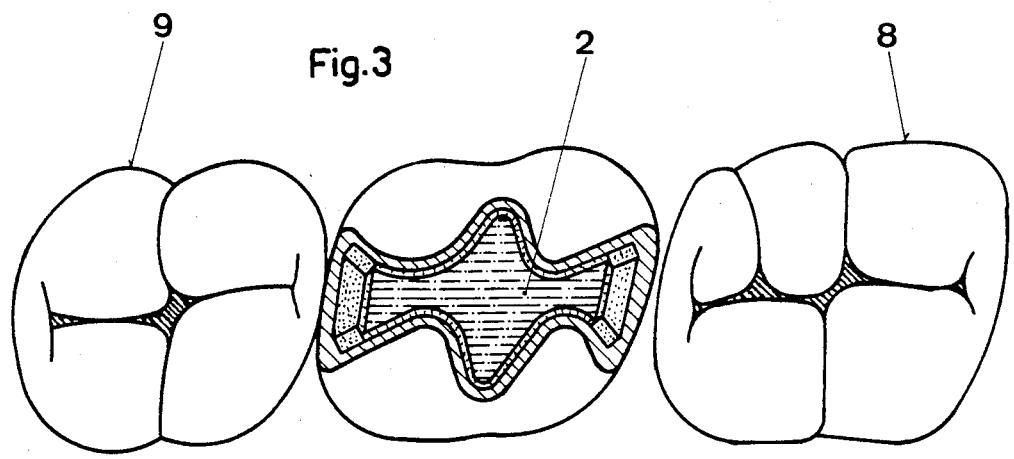
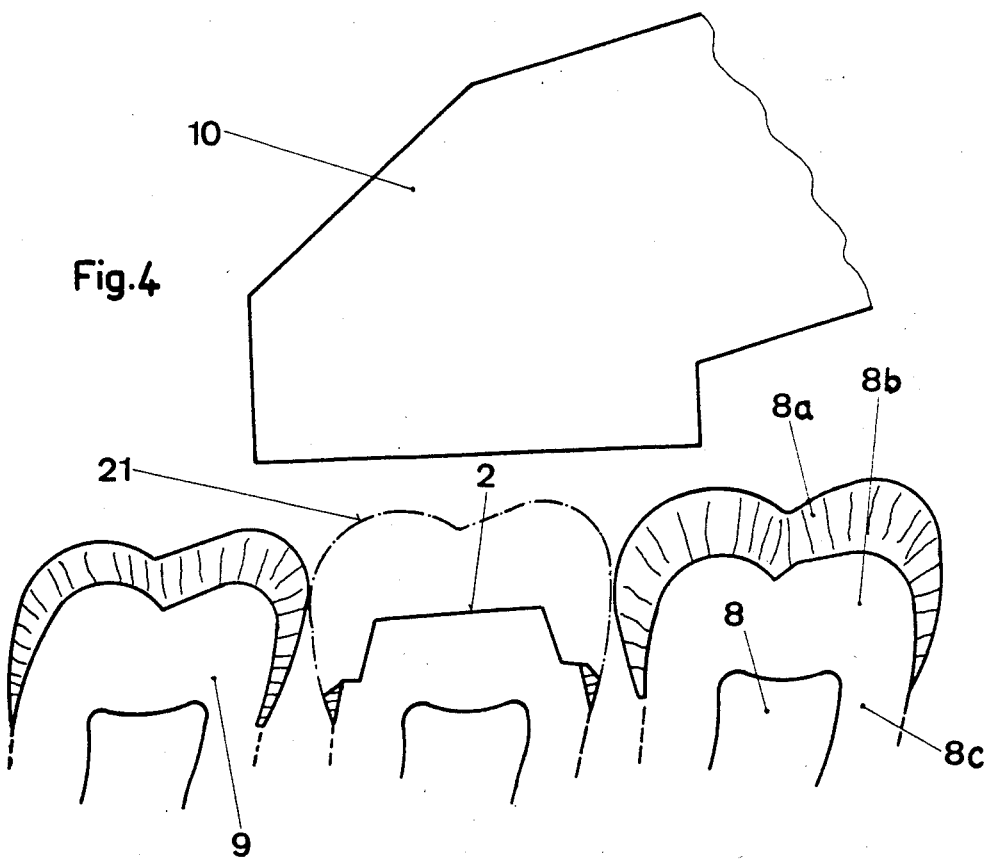

METHOD AND APPARATUS FOR THE FABRICATION OF CUSTOM-SHAPED IMPLANTS

This application is a continuation-in-part of U.S. Ser. No. 334,207, filed Dec. 24, 1981 and now abandoned.

FIELD OF THE INVENTION

This invention relates generally to a method for the fabrication of implants, for example a dental inlay.

BACKGROUND OF THE INVENTION

When incorporating alloplastic implants into organs, an exact fit is essential in order to ensure good retention and permanent support for the physiological stresses acting upon the underlying tissue, and to evenly distribute the forces acting upon the implant itself. The above is applicable, for example, to enossal and alveolar implants in the jaw, exoprosthetic contact lenses, hip joint prostheses, and also to the common dental alloplastic implants such as fillings, crowns and bridges. For enossal implants or contact lenses, the currently applied prosthetic devices are normally chosen from a kit containing various sizes, or else they are fitted to the organ after the organ has been trimmed to a standard shape.

In restorative dentistry, the established technique consists of the use of a custom-shaped implant such as can be produced by the conventional laboratory procedures. For the following description of the novel method, the dental scenario has been chosen by way of example.

Any kind of dental implant whose purpose is the permanent restoration of the tooth, particularly the crown of the tooth, to regain original appearance and function must be considered as alloplastic (i.e. a foreign body). The familiar techniques utilize fillings fabricated from precious cast metals, amalgam, ceramics or dental composite materials.

Conventional fillings in the form of inlays, onlays or overlays yield satisfactory physical properties and morphology, but a negative aspect is the generally high cost, especially when precious metals are used. The classic inlay fabrication, whether based on metal or ceramic filling materials, requires a string of time-consuming procedures such as: mold casting, model preparation, wax modeling, embedding of the wax model, die-casting, injection molding or stuffing, extrusion and high-temperature curing.

U.S. Pat. No. 4,182,312 teaches the reading of three-dimensional contour data of teeth and surrounding tissues directly inside the patient's mouth by means of a mechanical pantograph, in order to control a tool to fabricate the prosthesis, similar to a copy-milling machine. In order to read the contour data, a probe stylus rigidly connected to the pantograph must be manually guided along the contour of the tooth or gums. This procedure seems impractical, since a large number of translatory sweeps is required to faithfully survey the object under investigation, resulting in time consumption and discomfort to the patient. Another complication results from the need to compensate for the finite dimensions of the probe tip.

Furthermore, the need to establish a reference coordinate system results in temporarily fastening a tray to the patient's jaw, causing not only additional discomfort, but also restricting maneuverability of the probe. From a practitioner's point of view, these auxiliary devices and restrictions seem to be more cumbersome than the standard prosthetic methods involving the use of casts.

Besides the mechanical contour measurement taught in above-mentioned U.S. Pat. No. 4,182,312, several optical three-dimensional recording devices have been described in various publications including G. W. Butcher et al, "The Reflex Optical Plotter", Brit. Dent. J., 1981, 151, p. 304; E. M. Mikhail, Chapters 17–19 in "Photogrammetry", pp. 579–582, ed. F. H. Moffitt, Harper & Row, New York, 1980; and K. Takasaki, "Moiré Topography, Systems and Applications", Chapter 8 in "Handbook of Non-Topographic Photogrammetry", ed. H. M. Karara, Am. Soc. of Photogrammetry, Everybody Press, 1979. All of them, however, serve diagnostic purposes exclusively. The plotters used by Butcher and Mikhail require time-consuming operator assistance. Moiré Topography is a method for automatic contour mapping. It has, however, so far been limited (Takasaki 1979) to a coarse, nonabsolute depth measurement.

CONCEPT OF THE INVENTION

According to the invention, the established time-consuming techniques are replaced by a noncontact mapping of the relevant contours which is performed within a few seconds, either directly inside the patient's mouth or based upon a replica obtained from the region of interest. The prosthetic device, e.g. an inlay precisely conforming to the prepared dental cavity is then automatically prepared from a blank of raw ceramic or composite material, bypassing conventional restorative techniques.

More specifically, the invention is a method which involves the steps of noncontact topographic mapping of the natural contours of a body organ or of the surfaces, three-dimensional shapes and/or cavities artificially rendered into such organ and of the adjacent, untouched tissue contours by either directly scanning the contours or by scanning a replica of the contours; recording such contours utilizing a computing means and three-dimensional image processing techniques; designing and displaying a data set of the implant required to complement the organ under restoration; completing the data set of the implant by approximating the nonreadable parts necessary to describe a continuous, organ-restoring surface for the implant utilizing empirically determined curve sections fitted to the registered data; and fabricating an alloplastic implant from a material based upon the data set and a machining program, so that the implant optimally conforms to the interior and exterior surfaces of the body organ.

BRIEF DESCRIPTION OF THE DRAWINGS

FIG. 3 is a top view of a row of teeth;

FIG. 4 is a sectional side view of a row of teeth with an indication of the position of the scan-head;

DESCRIPTION OF THE PREFERRED EMBODIMENT

Figure 1:
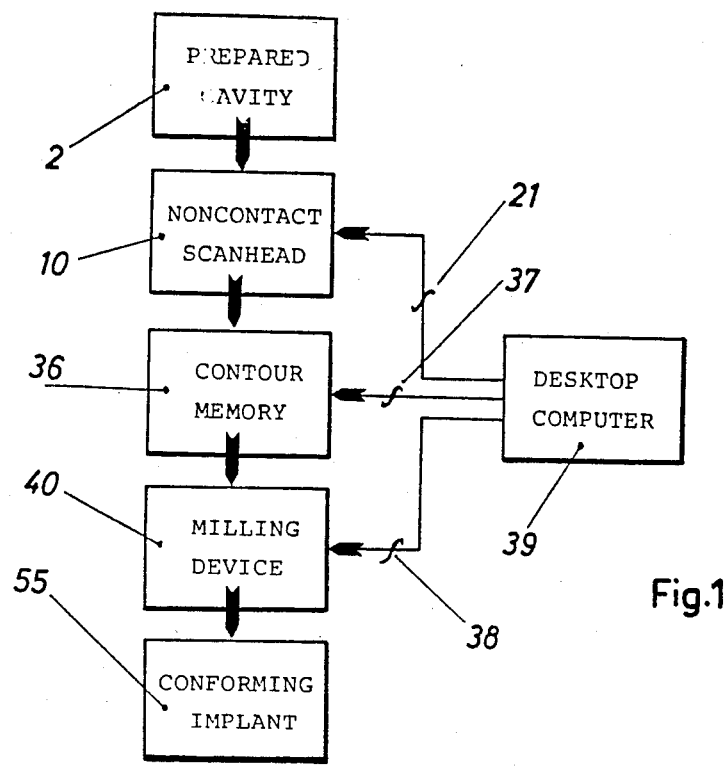
FIG. 1 is a flow-chart of the inventive implant fabrication process.

The inlay fabrication process is diagrammed in FIG. 1. The prepared cavity 2 is optically mapped by a non-contact scan-head 10. The scan-head 10 delivers the contour data, converted to electrical format, to be stored in the contour memory 36.

A desktop computer 39 controls the data acquisition and storage by means of the control signals 21, 37. The computer 39 reads the contour memory 36 following a line scan pattern. At the same time the milling device 40 is servoed to follow this pattern by means of position control signals 38.

The result of the milling operation is a custom-shaped implant 55 which exactly conforms to the prepared cavity 2.

Figure 2:
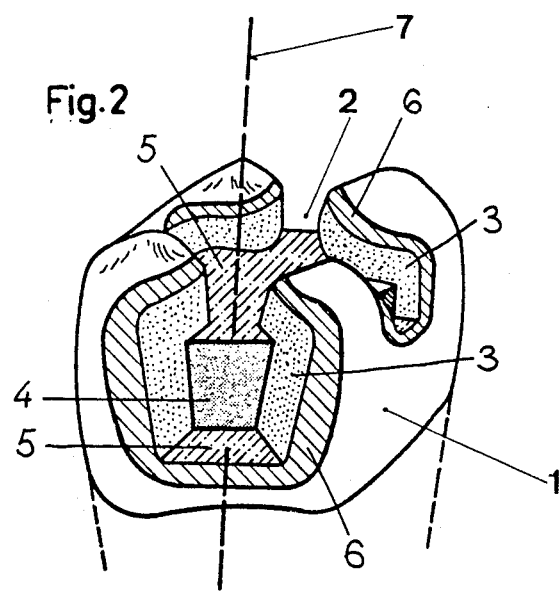
FIG. 2 is a perspective view of the crown of a tooth which has been prepared for an inlay insertion.

FIGS. 2 to 4 show situations encountered when applying the method to the restoration of a molar. FIG. 2 is a perspective view of the crown of a tooth 1 which exhibits a typical cavity affecting several sides of the tooth. The axial walls 3 and 4 form an angle of not less than 4 degrees with respect to an inlay insertion axis 7 which is approximately perpendicular to the occlusal plane. The bottom of the cavity is defined by the horizontal surfaces 5 while the outer edges 6 can be bevelled.

FIG. 3 is a top view of a contiguous mesioocclusodistal inlay cavity 2 with all walls showing. An adjacent mesial tooth 8 and distal tooth 9 complete the illustration.

FIG. 4 is a central, mesio-distal sectional view of the cavity 2 under restoration, bordered by mesial 8 and distal 9 neighbor teeth and with an indication of the scan-head location at 10. The different dental tissues include the external layer of enamel 8a, the dentine 8b and the pulp chamber 8c. The dot-dashed line points out the contour of the required restorative implant.

NONCONTACT SCAN-HEAD

Figure 5:
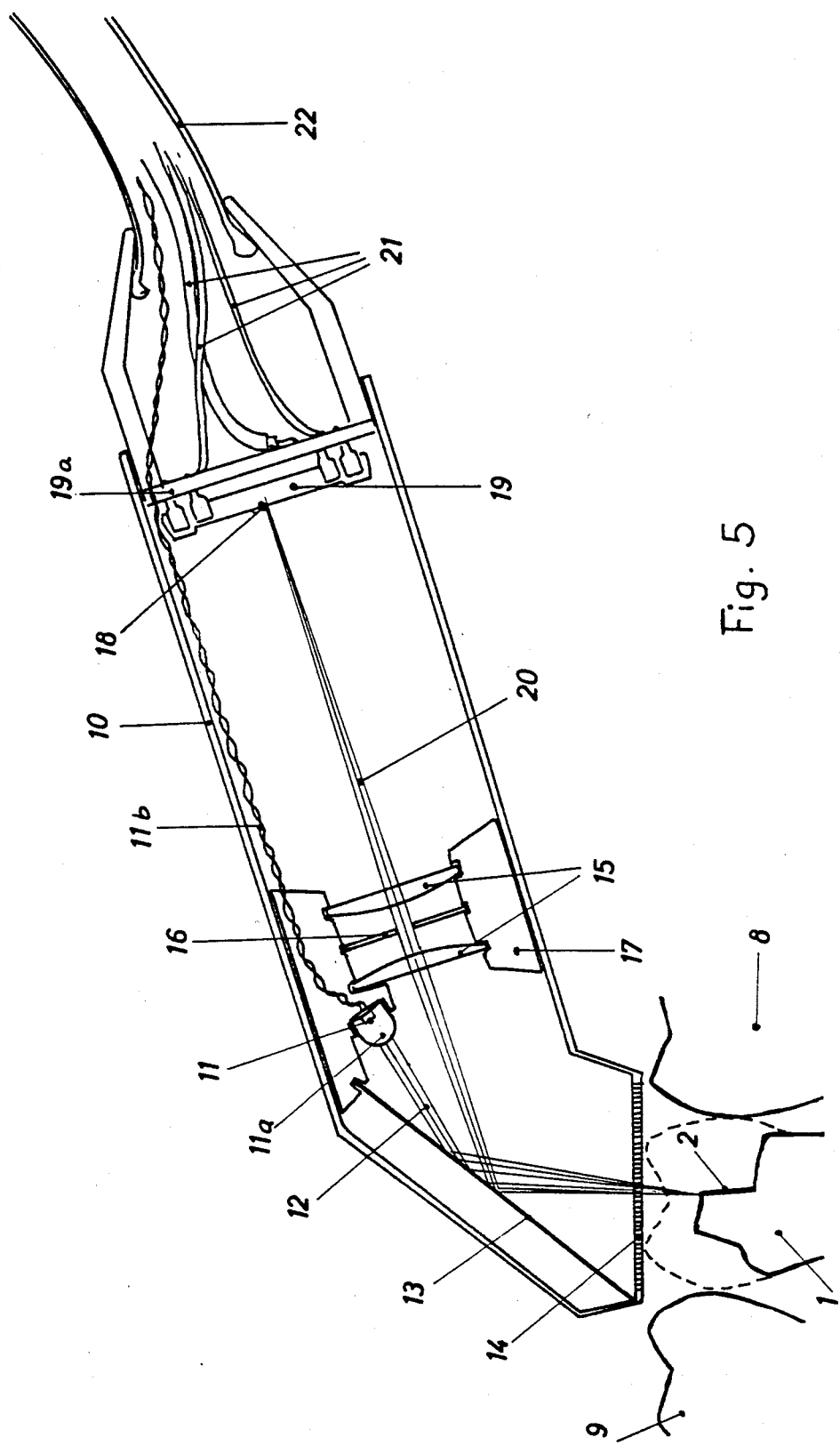
FIG. 5 is a schematic view of the scanhead with indication of the optical path.

Attention is now drawn to the embodiment illustrated in FIG. 5. A row of teeth 1, 8, 9 is placed under the scan-head 10 for noncontact mapping. Note, that the term "noncontact" refers to the process of actual depth determination. While no stylus or similar device physically traces the surface under investigation, the housing of the scan-head may well be in contact with oral tissue.

The function of the scan-head consists in providing contour data of the cavity 2 in ultimately electrical format. This is accomplished in the following manner: A light source 11, preferably a light emitting diode, with integral lens 11a radiates light onto the cavity 2. Before reaching the object the rays of light are reflected by a mirror 13. Its sole purpose is to allow easy acces to the patient's mouth by appropriately folding or bending the optical path 12, 20. The rays then pass through a ruling 14 (Edmund Scientific Corp. Barrington, N.J., part #030517). The function of the ruling 14 will be further described below.

The reflected light 20 is focussed by the aperture consisting of the lens 15, the stop 16 and the mounting 17 in order to produce an image 18 on the light sensor 19. The stop is chosen to provide adequate depth of field while maintaining enough lateral resolution. In the described embodiment a CCD solid state sensor (Fairchild Inc. Palo Alto, Ca., part #CD 221) has been mounted onto a printed circuit board 19a. The light sensor 19 converts the optical image to a series of raster lines of voltages corresponding to light intensity. This photoelectric process and scanning method is described in various publications e.g. Fairchild Charge Coupled Devices, CCD. copyright by Electronic 2000 for Fairchild USA. The timing signals utilized to control the sensor 19 can be taken from the commercially available unit CCD 2000C (Fairchild Area Camera Subsystem) or can be generated by dedicated electronics.

The scan-head is linked to the electronic unit by means of a cable 22, which contains leads 21 for timing signals and image information, as well as power leads 11b to the light emitting diode 11.

The scan-head thus generates electrical signals containing image information in a fashion much alike a television camera. We will now focus upon the particularities of the scan-head 10, namely the interaction of defined illumination, ruling 14 and aperture 15, 16 allowing the determination of 3-dimensional contour data.

DETERMINATION OF DEPTH

Figure 6:
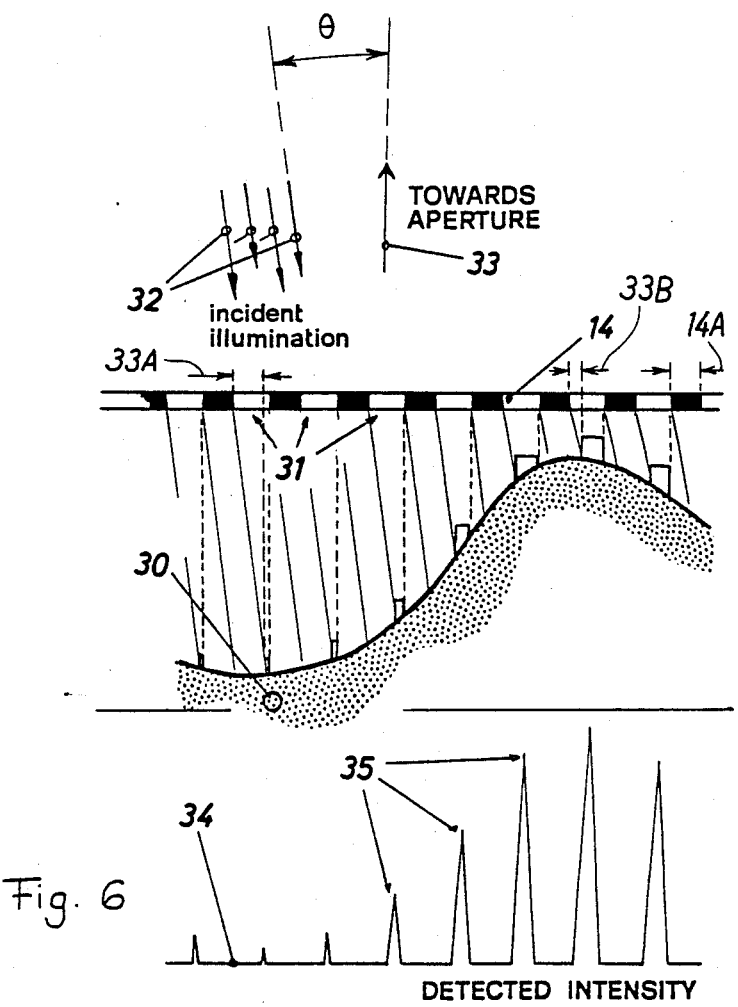
FIG. 6 is an illustration of the method of depth determination.

In the simplified situation, diagrammed in FIG. 6, an object 30 is placed underneath a ruling 14. When the object 30 is illuminated by a bundle of essentially parallel light rays 32, the ruling 14 casts a pattern of light and dark stripes onto the object 30.

The object 30 is then viewed under an angle $\theta$ different from the incident rays, such as indicated by the arrow 33, which points towards the aperture of a viewing system. Through the slits 31 of the ruling 14 now passes an amount of light proportional to the distance between each object point and the corresponding slit in the ruling 14. The intensity curve 34, depicted underneath the object, illustrates this proportionality. It is this intensity curve 34, which is produced by the scan-head 10.

More specifically, and as evident from FIG. 6, the light stripes produced from the light rays 32 by the ruling 14 are equally spaced in a direction which extends approximately perpendicular to the rays 32 and parallel to the plane of the drawing. When the pattern of light stripes on the object 30 is viewed in a direction parallel to the arrow 33, however, each light stripe will have an apparent positional shift in a direction which extends perpendicular to the arrow 33 and parallel to the plane of the drawing, or in other words rightwardly in FIG. 6. The amount of the shift at each point along each light stripe is proportional to the vertical height of the corresponding portion of the surface on the object 30. Consequently, when the pattern of stripes is viewed parallel to the arrow 33 and through the windows or slits 31 of the ruling 14, the amount of light passing through any given portion of each slit 31 is proportional to the actual level of the corresponding region of the contour on the object 30. A necessary condition for ensuring this proportional relationship between intensity and distance is that, as evident from FIG. 6, the reflection of any given light stripe of the pattern is visible in whole or in part only through a single corresponding slit 31, which in turn will be true only if the width 14A of the opaque region between adjacent slits 31 is greater than the difference between the maximum positional shift 33A and the minimum positional shift 33B.

The intensity curve 34 is now sampled, each data point 35 is represented by an 8 bit binary value. Since each point of the image is thus converted, the image- or contour memory 36 holds the complete contour of the cavity 2.

While the accuracy of the readings obtained with the scan head are generally adequate for their intended purposes, they can, if desired, be improved somewhat by the optional step of coating the tooth with a layer of a white, glarefree substance. A suitable substance for this purpose is commercially available under the name CAVISOL, and is made by Svedia Dental Industry of Enkoeping, Sweden. CAVISOL not only provides substantially uniform contrast at various locations across the tooth, but also includes an antibacterial substance which helps to prepare the cavity in the tooth for permanent installation of the implant. CAVISOL can be applied in any convenient manner, for example with a swab, a toothpick, or an airbrush.

Because the range of intensities is not originally known, an initial calibration is needed to precisely scale the transfer formula: intensity-depth. This calibration can be accomplished by mapping a standard object, which has been measured utilizing conventional techniques e.g. calipers. Once this calibration has been performed, the image memory 36 can be organized to represent the contour on a 0.05 mm raster, thus covering a total volume of 12.8×12.8×12.8 mm actual length.

For the embodiment described here, the memory has been built by using two commercially available boards (Matrox Ltd. Quebec, Canada, part #RGB 256/4).

During the course of the actual milling process a pair of counters keep track of the x/y location of the memory. These coordinates are transferred to the stepper motors and corresponding translatory stages. The z coordinate for the milling tool is the data found in each x/y memory location. Control of the milling process, the memory addressing and display as well as providing the timing signals for the scan-head 10 can be accomplished by a desk top computer (e.g. Apple II, Apple Inc., Cupertino, Ca.) 39, which is connected to the respective units by signals 21, 37 and 38 of FIG. 1.

So far, the milling operation has been oversimplified, since the size of the diamond bur 51 has not been accounted for. The point of the bur 51 is of essentially cylindrical shape. Therefore we retrieve from the contour memory 36 all data points, which would be touched by the cutting edge of the bur 51. These points fall on a circle, whose diameter is given by the diameter of the bur 51. The data point exhibiting the minimum depth is then identified and its z value determines the z position of the bur 51.

THE MILLING DEVICE

Figure 7:
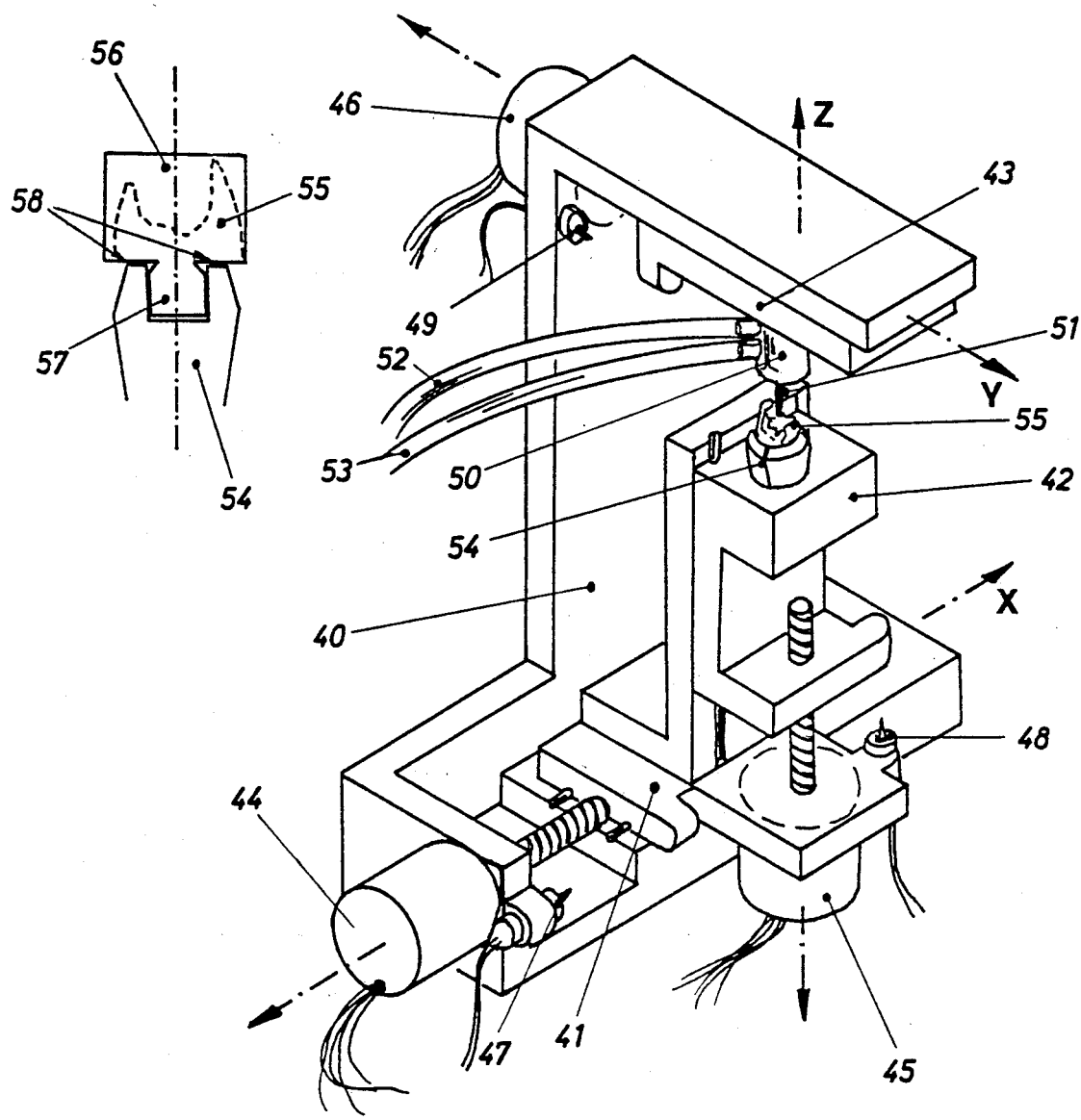
FIG. 7 is a basic arrangement of the milling device.

This device is essentially a numerically controlled (NC) milling machine. A description, at this point, seems, however, appropriate due to the special purpose of this apparatus. The operation of the milling device is illustrated in FIG. 7.

On a supporting frame 40 are mounted three translatory stages or platforms 41, 42, 43, which platforms are normally positionable on end with respect to the coordinates x, y and z. The translatory platforms are each connected to the shaft of a stepper motor 44, 45, 46 by means of a lead screw. A good example of such a stage or platform is "Micro Controle" type MR-80.25, part #338404. M.C. Corp. Vitry-sur-Seine, France. For each axis a stepper motor (Sigma instruments mod. 20-2220 BD 200) drives the respective lead screw.

Since a stepper motor only allows incremental positioning, absolute location is determined as follows: A limit switch, 47 resp. 48, 49 establishes the zero position. By keeping track of the number of steps applied to each motor and the sense of rotation, absolute position is always known to the system.

As the figure further illustrates a high speed turbine 50 (Midwest American, Melrose Park, Ill. part #464006), powering a diamond bur 51, is rigidly connected to the y axis stage 43. This turbine 50 is energized by means of an air hose 52. The necessary coolant is supplied by an additional tube 53. These tubes 52, 53 are connected to the drill control unit found in every dental practice.

Mounted on the z translatory stage 42 is a three jaw chuck 54, which firmly grips the work piece 55 during the fabrication process. The blank 56, out of which the implant 55 is to be fabricated is of basically cylindrical shape. As further illustrated, in the insert, a nipple 57 is provided at one end of the blank 56 ensuring positive retention. This particular fabrication arrangement leaves the occlusal side 58 of the inplant 55 unfinished. This represents no further problem, as this area has to be manually finished by the dentist after the implant has been cemented into place and the nipple cut or broken off.

By way of example the milling machine has been described assuming three degrees of freedom (x, y, z). The principle can, however, be extended to a more complex situation, and the method claimed should not be considered limited in this feature.

ALTERNATIVE EMBODIMENTS

Figure 8:
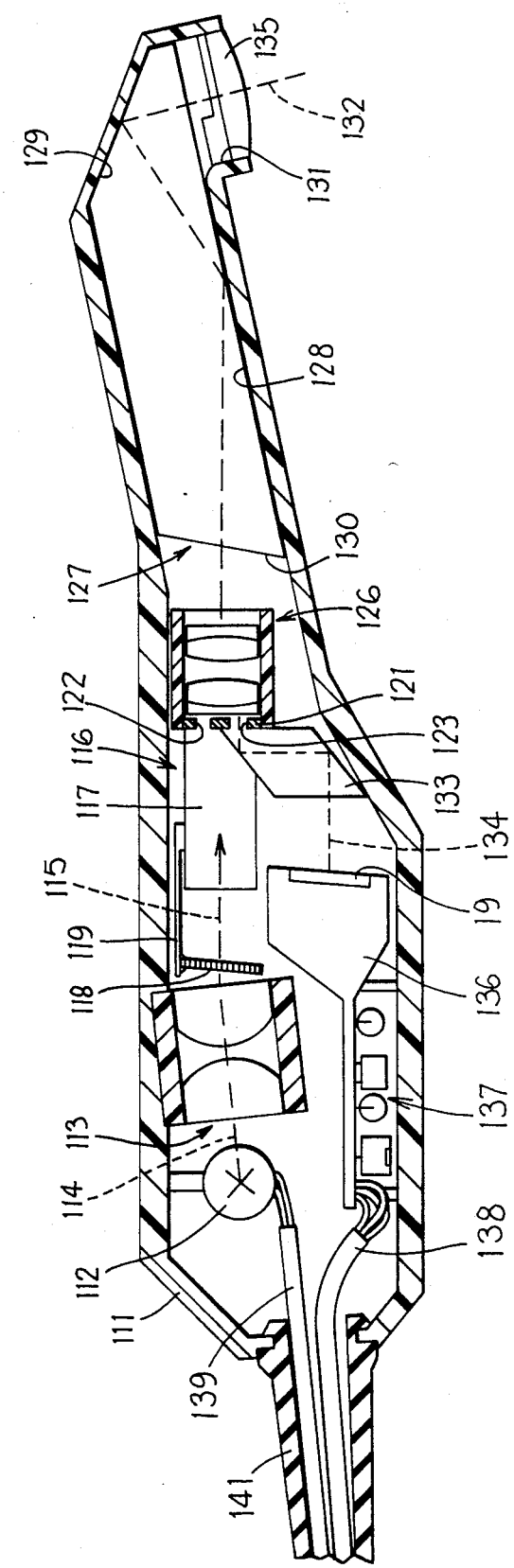
FIG. 8 is a diagrammatic sectional view of an alternative embodiment of the scan head of FIG. 5.

FIG. 8 illustrates an alternative embodiment of the scan head of FIG. 5. The scan head of FIG. 8 measures depth using the same basic principles as the scan head of FIG. 5, but includes a somewhat different arrangement of components.

More specifically, the scan head 110 of FIG. 8 includes an elongate housing 111 and a light source 112 which is supported within the housing 111 adjacent one end thereof. A condensing lens arrangement 113 is supported in the housing 111 adjacent the light source 112, and light from the light source 112 travels through the condensing lens arrangement 113 along a path 114. A beam splitter arrangement 116 is supported approximately centrally within the housing 111, and has a portion 117 which extends toward the condensing lens arrangement 113. A ruling or optical plate 118 is fixedly supported at one end of an elongate support 119 which has its other end fixedly supported on the portion 117 of the beam splitter arrangement 116. The ruling 118 is similar to the ruling 14 of FIG. 5 and is a translucent plate having thereon a plurality of parallel, spaced, opaque ruling lines. The ruling 118 is adjacent the condensing lens 113, and extends almost, but not exactly, perpendicular to the path of travel 114 of light leaving the condensing lens 113. In the preferred embodiment, the ruling 118 is arranged at an angle of about 80° with respect to the path of travel 114. The light then travels from the ruling 118 to the beam splitter 116 along a path of travel 115 which forms an angle of about 85° with respect to the ruling 118. The beam splitter 116 includes an aperture stop plate 121 at the end thereof remote from the light source 112, and the plate 121 has two vertically spaced holes 122 and 123 therein and is adjacent an image-forming lens arrangement 126. A prism 127 is provided in the right end of the housing 112, and has two reflective surfaces 128 and 129 thereon which reflect light emitted from the image-forming lens arrangement 126 so that it passes out of the scan head 110 through an opening 131 at the right end of the housing 111 along a path of travel 132. The prism 127 could, of course, be replaced by two mirrors, or some other functionally equivalent structural arrangement.

The left end surface 130 of the prism is arranged at an angle of about 80° with respect to the path of travel of light entering the prism 127. A telecentric field lens 135 is provided in the opening 131. Light emitted through the opening 131 and reflected by an object such as a tooth which is being scanned reenters the scan head 110 along the path 132, is reflected by the surfaces 129 and 128, and passes through the image-forming lens arrangement 126 and the lower hole 123 of the aperture stop plate 121. The beam splitter arrangement 116 includes a prism portion 133 having two parallel reflective surfaces which twice reflect light passing through the lower hole 123 and direct it along a path 134 to a sensor 19, which is arranged at an angle of about 85° with respect to the path 134. The sensor is identical to the sensor 19 shown in FIG. 5 and is removably supported in a socket 136, the socket 136 being in turn connected to a circuit 137 which includes conventional line driver and line receiver arrangements for coupling the sensor 19 on the socket 136 to a control circuit at a remote location through wires 138 which exit the housing 110 through a flexible rubber grommet 141. Power for the light source 112 is supplied by wires 139. The reason the ruling 118, prism surface 130 and sensor 19 are not precisely perpendicular to the path of travel of light therethrough is to minimize the effects of any internal reflections of light therefrom.

The scan head 110 of FIG. 8 operates as follows. Light from the light source 112 passes through the condensing lens arrangement 113, ruling 118 and portion 117 of the beam splitter 116 along the paths 114 and 115. This light then passes through the upper opening 122 of the aperture stop plate 121, through the image-forming lens arrangement 126, through the prism 127, through the field lens 135 and onto a tooth along the path 132. The ruling 118 produces an intensity pattern which is a series of parallel stripes and is projected onto a tooth in a manner similar to that shown diagrammatically in FIG. 10. Light reflected from the tooth along the path 132 passes through the field lens 135, the prism 127, the image-forming lens arrangement 126, and the lower hole 123 of the aperture stop plate 121, and the portion 133 of the beam splitter 116 then directs the light onto the sensor 19. The sensor 19 includes a two dimensional array of horizontal rows and vertical columns of sensor elements which each correspond to a respective pixel of a video image produced by the sensor 19. If a planar surface oriented perpendicular to the path 132 is held adjacent the scan head, each of the light stripes of the intensity pattern reflected by the surface will, after passing through the prism 127, lens arrangement 126, aperture stop plate 121 and beam splitter 116, impinge substantially directly on a respective row of sensor elements on the sensor 19. If the surface is then slowly moved away from the end of the scan head in a direction parallel to the path 132, the parallax between the projected and reflected light, resulting from the spacing between the two holes 122 and 123 of the aperture stop plate 121, will cause the reflected stripe pattern to slowly move vertically on the sensor 19, the vertical shift of each individual stripe being a direct measure of depth. In other words, as a given point on the surface moves further away from the scan head, the amount of light reflected from the region of this point which strikes a respective sensor element of the sensor 19 is modulated in a predetermined fashion. Thus, the intensity of light detected by each sensor element is a direct measure of the distance between the scan head and a corresponding point on an object being scanned.

As evident from FIGS. 5 and 8, the scan head 110 of FIG. 8 differs from the scan head 10 of FIG. 5 in that the ruling 118 in the embodiment of FIG. 8 is located near the light source 112, and light reflected back into the scan head 110 from an object being scanned does not pass through the ruling 118 a second time. The inherent vertical spacing between the horizontal rows of sensor elements on the sensor 119 in effect functions as a second ruling.

Figure 9:
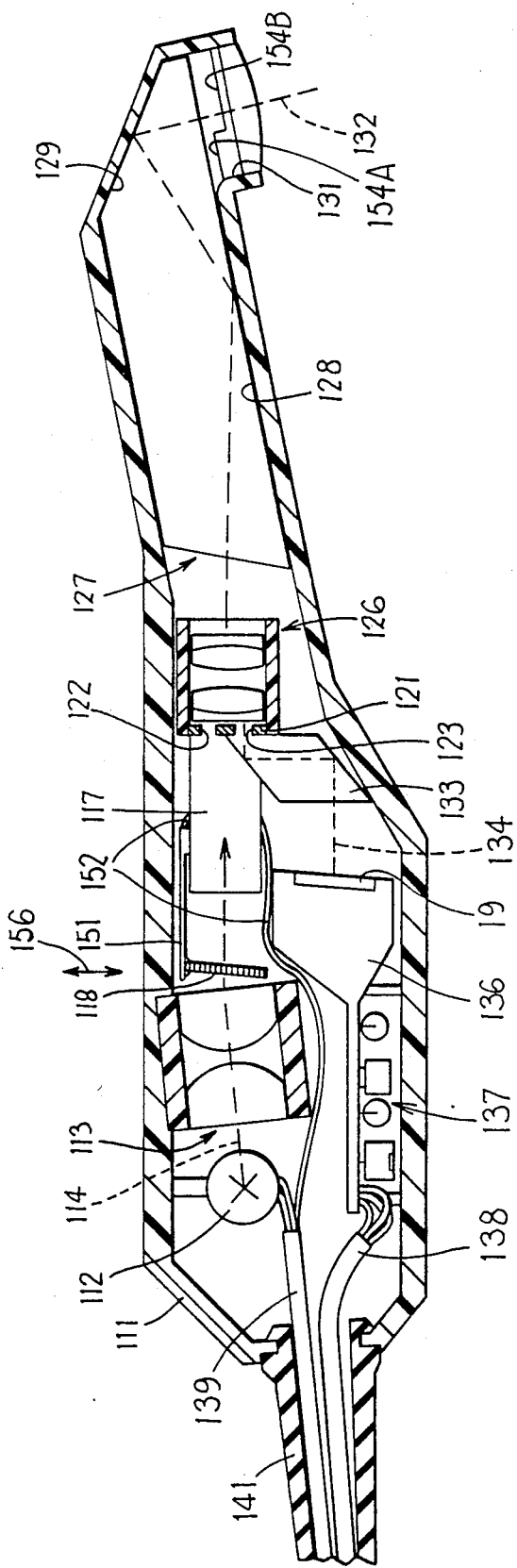
FIG. 9 is a view similar to FIG. 8 of an alternative embodiment of the scan head of FIG. 8.
Figure 10:
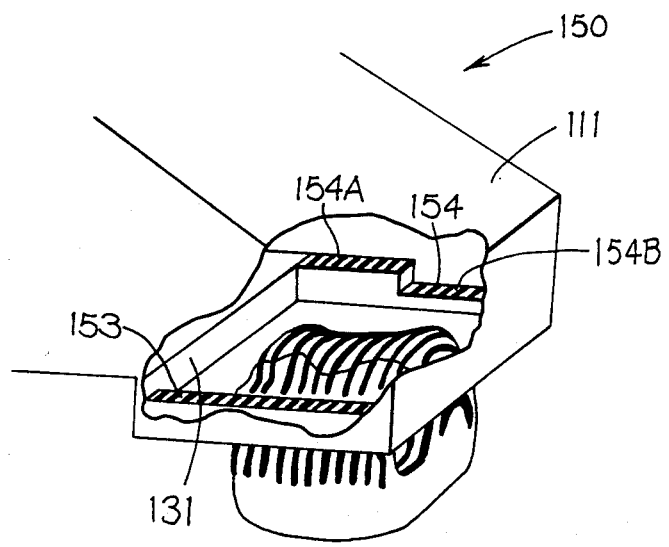
FIG. 10 is a fragmentary diagrammatic view of the scan head of FIG. 9 in use.

Although the scan heads shown in FIGS. 5 and 8 each provide readings which in general are sufficiently accurate for purposes of the present invention, small nonuniformities may be present. For example, two sensor elements of the sensor 19 may have slightly different sensitivities to light, and different points on the object being scanned may have slightly different light reflection characteristics. FIGS. 9 and 10 illustrate a scan head 150 which can be utilized to obtain slightly more accurate readings than the scan heads of FIGS. 5 and 8.

Figure 11:
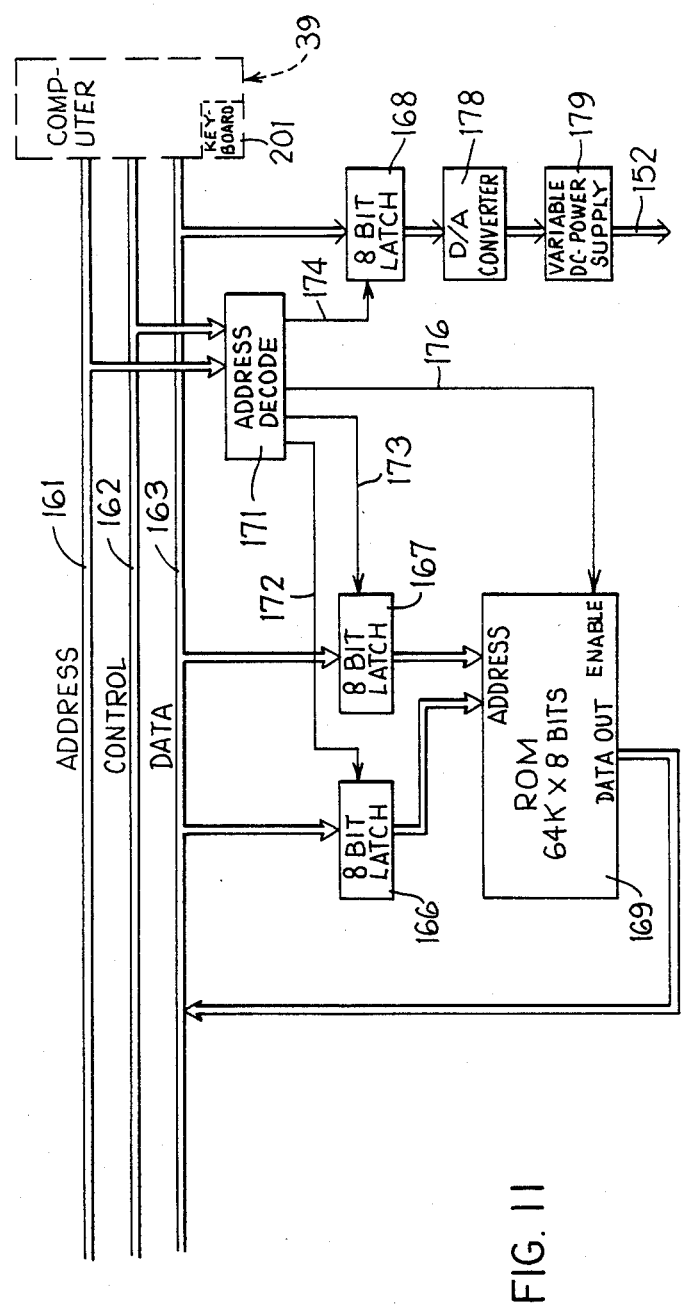
FIG. 11 is a schematic block diagram of support circuitry for the scan head of FIG. 10.

More specifically, FIGS. 9 and 10 illustrate the scan head 150, which is a modified version of the scan head 110 of FIG. 8, and FIG. 11 illustrates support circuitry for the scan head 150. The scan head 150 is identical in most respects to the scan head 110. Identical parts have therefore been identified with the same reference numerals, and only the structural differences will be described in detail.

In particular, the ruling 118 in the scan head 150 is supported on the portion 117 of the beam splitter 116 by an elongate support element 151 which is a piezoelectric component manufactured by Philips, and available from Philips GmbH in Hamburg, Germany, as Part No. 4322 020 07400. A description of this component has appeared in the German magazine "Feinwerktechnik & Messtechnik" (Feinwerktechnik & Messtechnik 90 (1982) 7, page 364). Wires 152 are connected to the right end of the piezoelectric element 151 for applying a voltage thereto. When a voltage is applied to the element 151, it will effect a small amount of curvature along the length of the element 151, thereby causing the left end of the element 151 to move vertically a small distance, the direction and amount of vertical movement corresponding to the polarity and amplitude of the voltage applied. This will cause the ruling 118 to be deflected vertically, as indicated by arrow 156. The reason for this deflection will be discussed in more detail below.

The scan head 150 also has inwardly facing reference surfaces 153 and 154 (FIG. 10) on opposite sides of the opening 131. The reference surface 154 has two portions 154A and 154B, and the surfaces 153, 154A and 154B are each planar and substantially perpendicular to the path 132 of light leaving the scan head 150.

As shown in FIG. 11, the computer 39 has conventional address, control and data buses 161, 162 and 163. Three conventional eight-bit latches 166, 167 and 168 each have their data inputs connected to the data bus 163 and are each treated by the computer as a respective location of its memory. The data outputs of the latches 166 and 167 are connected to respective address inputs of a 64K word by 8-bit read-only memory (ROM) 169, and the data outputs of the ROM 169 are connected to the data bus 163. A conventional address decode arrangement 171 made of conventional combinational logic components is connected to the address and control buses 161 and 162 and, when the address and control buses 161 and 162 indicate that the computer 39 is initiating a load of data into a selected one of the latches 166-168, the address decode arrangement 171 places a signal on a respective one of three load lines 172, 173 or 174 which causes the associated latch 166, 167 or 168 to accept a word present on the data bus 163 and to hold this word until such time as a further word is loaded into it by the computer 39. The ROM 169 is also assigned one memory address, and the computer 39 can read data from the ROM 39 by selecting this memory address. In particular, the address decode arrangement 171 will, when it detects that the computer 39 is initiating a read of this location, produce a read signal on a line 176 which enables the outputs of the ROM 169 and causes it to place on the data bus 163 the data word which is stored in the location addressed by the latches 166 and 167.

The data outputs of the latch 168 are connected to inputs of a conventional digital-to-analog converter 178, which in turn has its outputs connected to control inputs of a conventional variable DC power supply 179. The outputs of the variable supply 179 are connected to the wires 152 which, as described above, are connected to the piezoelectric element 151 (FIG. 9) in the scan head 150. By loading one of four predetermined binary numbers in the 8-bit latch 168, the computer 39 will cause the power supply 179 to generate a selected one of four voltages which, when applied to the piezoelectric element 151, will cause the ruling 18 to be moved vertically (arrows 156) to one of four predetermined positions. These positions are spaced from each other by a distance equal to one-fourth of the distance between two adjacent lines or rulings on the ruling 118. Since the vertical movement of the ruling effects a vertical movement of the intensity pattern, the respective positions of the ruling 118 will, for convenience, be referred to by the phase shift imparted to the intensity pattern. More specifically, the initial position shown in FIG. 9 corresponds to a phase shift of 0°, a vertical shift to the next position by a distance of one-quarter of the spacing between two adjacent lines on the ruling corresponds to a phase shift of 90°, a further shift to the next position by this same distance corresponds to a phase shift of 180°, and a still further shift by this distance to the next position corresponds to a phase shift of 280°.

The scan head 150 is utilized in the following manner. With the ruling 118 in its 0° position, the scan head 115 is manually positioned relative to a tooth or other object to be scanned, and the operator then pushes a button, for example on a keyboard 201 (FIG. 11) of the computer, to tell the computer 39 to proceed. The computer 39 will then read from the contour memory 36 (FIG. 1) and store in its own memory a digitized video image based on data from the sensor 19, and will then load a predetermined 8-bit word into the latch 168 to cause the ruling 118 to move to its 90° position. The computer will thereafter read a second digitized video image and store it in its memory, move the ruling 118 to its 180° position, read a third image and store it in memory, move the ruling 118 to its 270° position, and read a fourth image and store it in memory. The time required to read these four images is a sufficiently small portion of a second so that no significant manual movement of the operator can occur. Each of the four images stored in memory will be a 256-by-256 array of 8-bit words, each word corresponding to a respective pixel of the associated video image, the binary number in each word corresponding to the light intensity measured by the corresponding sensor element of the sensor 19. The computer will then process these four images in the following manner.

The 180° image will be subtracted from the 0° image in a pixel-by-pixel manner by reading a binary number from a respective word of the 180° image, subtracting it from the number in the corresponding word of the 0° image, and then placing the result back in the work of the 0° image. In a similar manner, the 270° image is subtracted from the 90° image. The result of these two subtractions is thus two differential images in the memory of the computer which will be respectively referred to as the 0°-180° image and the 90°-270° image. Each of these subtractions will eliminate any fixed offset present in the intensity measurements at any given sensor element, thereby assuring that each differential is a uniform measure of the difference in intensity of the light reflected from a single location on the object being scanned for two different positions of the ruling 118 which are spaced by a phase shift of 180°. In other words, if one sensor element is slightly more light sensitive than a second sensor element, intensity readings from the first sensor element for a given amount of light will each be slightly greater than intensity readings from the second sensor element for the same amount of light, but when two respective readings of different intensity for each sensor element are subtracted, the differential for the first sensor element will be substantially identical to that for the second.

It should be evident that the 0°-180° image in the memory of the computer 39 effectively leads the 90°-270° image in phase by 90°. Thus, for any given pixel, the two numbers stored in the corresponding locations of the two images can be treated as the real and imaginary parts of a complex vector. The phase angle of this vector is proportional to the distance between the scan head and the associated location on the object being scanned. This phase angle is computed by performing a rectangular-to-polar conversion for each of the pixels in the stored images, each resulting phase angle being written into the corresponding location of the 90° image, which is no longer needed.

The rectangular-to-polar conversion can be carried out in any conventional manner. In the present invention, the 8-bit number from a location of the 0°-180° image is written into the 8-bit latch 166 (FIG. 11) and the number from the corresponding location of the 90°-270° image is written into the latch 167. For any two words loaded into the latches 166 and 167, there is a unique phase angle, and an 8-bit binary number representing this phase angle is stored in the location of the ROM which will be addressed by these two words. Thus, after loading the latches 166 and 167, the computer reads the output of the ROM 169 by causing the address decode arrangement 171 to produce a read signal on the line 176 to cause the ROM to place the binary number representing the appropriate phase angle on the data bus 163, and the computer then stores this number in its memory. As mentioned above, each phase angle in the resulting phase angle video image is proportional to the distance between the scan head and the associated location on the object being scanned. Each phase angle is now converted into the corresponding distance in the following manner.

The reference surfaces 154A and 154B (FIG. 19) are vertically spaced by a predetermined distance, which in the preferred embodiment is 3 millimeters, and an edge portion of the intensity pattern is projected thereon, as shown in FIG. 10. Light reflected from the reference surfaces 154A and 154B is directed onto the sensor 19, and an edge portion of each image read from the sensor 19 thus represents the surfaces 154A and 154B. Thus, by selecting two phase angles from the phase angle image in its memory, which respectively correspond to locations on the surfaces 154A and 154B, and by then subtracting one of these phase angles from the other, the computer will obtain a scaling factor S which represents the difference in phase corresponding to the distance between the surfaces 154A and 154B. The computer can then, for each phase angle in the phase angle video image, subtract from the measured phase angle the phase angle measured for the location on the surface 154A and then multiply the result by 3/S, thereby obtaining the distance in millimeters from a plane containing the surface 154A to the corresponding location on the object being scanned. Each such product is stored in the corresponding location of the contour memory 36. Thereafter, the video image in the contour memory 36, which is derived from four separate images and is thus less subject to sensor and object irregularities than a single image read directly from the scan head, is utilized by the computer 39 to control the milling device 40 in a manner similar to that applicable to the embodiment of FIGS. 1 through 5.

Figure 12:
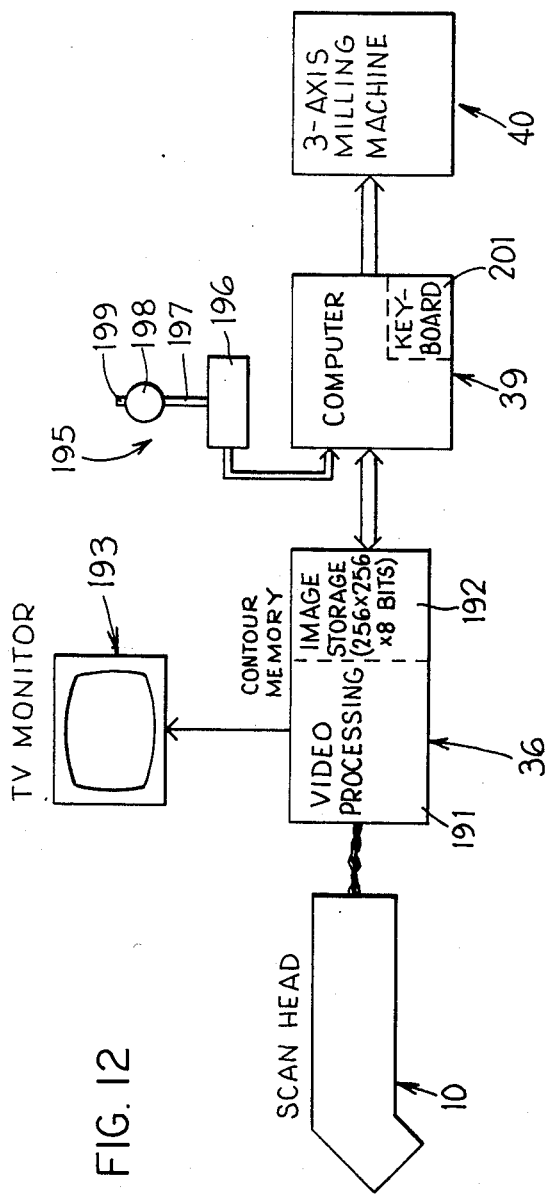
FIG. 12 is a block diagram of a system which embodies yet a further feature of the invention.

FIG. 12 illustrates a further feature of the invention embodied in a modified version of the system of FIG. 1. In general, the system includes the basic components illustrated in FIG. 1, including the scan head 10, contour memory 36, computer 39 and milling machine 40. The contour memory 36 includes a 256-by-256 array of 8-bit words which serves as a video image storage area 192, and conventional video processing circuitry which can convert an image from the scan head 10 into digital data, store it in the image storage area 192, and display the stored image on a conventional television monitor 193.

A conventional joy stick device 195 includes a base 196 having an upright control stick 197 thereon which is movable in two dimensions and has a handle 198 at the upper end thereof, the handle 198 having a manually operable push button 199 thereon. The joy stick 195 is connected to the computer 139 in a conventional manner. The joy stick 195, the manner in which it is connected to the computer 39, and the software required to convert data from the joy stick 195 representing the position of the control stick 197 into a corresponding position in a video image is well known, for example from the video game art, and is therefore not described in detail.

After the video processing circuitry 191 of the scan head 10 has stored a video image in the image storage area 192, and before the computer 39 uses this data to cause the milling machine 40 to prepare a corresponding implant, the joy stick 195 is used by the system operator to effect some simple modifications of the data which is stored in the contour memory 36 and is displayed on the monitor 193.

More specifically, the operator first positions the control stick 197 at an edge of its range of movement which corresponds to the right or left edge of the screen 193, and then pushes the button 199. When the button 199 is pushed, the computer will zero the location in the image storage area 192 of the contour memory 36 which corresponds to the position of the control stick 197, the zero in that memory location will thereafter cause the corresponding pixel on the screen of the monitor 193 to be displayed with maximum brightness. Thus, as the control stick 197 is moved with the button 199 pushed, its path of movement will be stored in the contour memory 36 as a series of zeroed locations and will be displayed as a bright line on the monitor 193.

The image displayed on the monitor 193 is such that the operator can visually recognize the edges of the cavity in a tooth, or in other words the edges 6 of the cavity illustrated in FIG. 2. The operator then moves the control stick 197 so that the bright trace appearing on the screen moves inwardly from the side edge of the screen until the edge of the cavity has been reached, and then moves the control stick 197 so as to trace the outline of the cavity. The cavity will thus be outlined on the monitor 193 by a bright trace.

The operator then presses a button on the keyboard 201 of the computer 39 to tell the computer to proceed, and then the computer will automatically zero all of the locations in the contour memory which correspond to pixels falling outside the cavity in the tooth, for example by starting at the left and right edges of the image and zeroing successive pixels in each row of pixels in a direction toward the center of the image until a pre-existing zero is encountered, each such pre-existing zero being one created manually by the operator using the joy stick 195.

Thereafter, the computer will automatically proceed to utilize the data in the contour memory 36 to operate the milling machine 40 to create the implant for the cavity in the tooth. Since the locations in the contour memory 36 which represent the contours of the cavity have not been changed, the proper implant will still be machined exactly as it would be in the embodiment of FIGS. 1–5. However, in view of the fact that the numbers stored in the contour memory 36 control movement of the milling tool along its Z-axis, the zeroes in the locations in the memory external to the cavity will cause the milling tool to be moved to its maximum depth in these regions, thereby machining away a substantial amount of excess material which might otherwise have to be manually removed by the dentist after the implant has been cemented in place.

SUMMARY

Summarizing, the present invention provides the dentist, among others, with means to accurately map, store and display the contour of a tooth prepared for inlay restoration, and alleviates conventional casting methods. A machine located near the operating site fabricates the customized implant according to the stored contour data by cutting, milling or eroding a blank of filling material. The implant therefore becomes immediately available for insertion by the dentist.

The method of the invention allows fabrication of alloplastic implants of the medical or dental kind, using well-defined materials and a highly controlled process, by making use of a combination of state-of-the-art photogrammetric and digital storage, display and computing as well as NC cutting techniques.

This results in a substantial quality increase along with reduced cost for medical and dental restorations.

The embodiments of the invention in which an exclusive property or privilege is claimed are defined as follows:

1. A method for facilitating the fabrication of a workpiece to be placed onto a light reflective object having a three dimensional contour thereon to which said workpiece is to be conformed, comprising the steps of:
   noncontact topographic scanning of said contour on said object, including the step of directing a predetermined intensity pattern of light onto said contour so that a corresponding intensity pattern of light will be reflected therefrom, the varying intensity pattern of said reflected light being a measure of said three dimensional contour on said object;
   directing said pattern of said reflected light from said object onto a light sensing means;
   converting said pattern of light on said light sensing means into a corresponding pattern of electrical data;
   selecting a set of said electrical data;
   storing said set of said electrical data;
   mounting said workpiece onto a machining means which is responsive to electrical data sequentially presented thereto;
   sequentially presenting said stored set of electrical data to said machining means; and
   machining said workpiece into a three dimensional shape in accordance with said stored set of data.

2. The method according to claim 1, wherein said object is a human tooth and said three dimensional contour is a cavity therein.

3. The method of claim 1, wherein said noncontact topographic scanning is done optically.

4. The method according to claim 1, including after said storing step and prior to said sequentially presenting step the step of modifying said stored set of said electrical data.

5. The method according to claim 1, including prior to said scanning step the step of applying to said contour on said object a coating of a glarefree, reflective substance.

6. The method according to claim 1, wherein said step of directing said predetermined intensity pattern onto said contour includes the steps of: causing said predetermined intensity pattern to travel toward said contour in a first direction and said pattern of reflected light to travel away from said contour in a second direction oriented at an angle to said first direction; using as said predetermined intensity pattern a pattern of light which includes alternating bright and dark regions uniformly spaced in a third direction extending perpendicular to said first direction and parallel to a plane containing said first and second directions, said contour causing portions of said bright and dark regions to be spatially shifted in said reflected pattern of light in a fourth direction extending perpendicular to said second direction and parallel to said plane containing said first and second directions; and selecting the width of each said dark region between adjacent said bright regions of said predetermined intensity pattern to be greater than the difference between the maximum and minimum amounts of spatial shift caused by respective points on said contour which are spaced the maximum possible distance from each other in said second direction; and wherein said converting step includes the step of causing said light sensing means to measure the average light intensity of portions of said pattern of reflected light in each of a plurality of predetermined and stationary window regions which are uniformly spaced from each other in said fourth direction and which each have a predetermined width in said fourth direction, the intensity measured in each said window region being proportional to the actual physical position in said second direction of a corresponding portion of said contour.

7. An apparatus for facilitating the fabrication of a workpiece to be placed onto a light reflective object having a three dimensional contour thereon to which said workpiece is to be conformed, comprising:
   housing means;
   light source means on said housing means and first directing means for directing the light from said light source means toward said contour;
   optical plate means on said housing means interposed in the path of said light from said light source means for controlling the magnitude of said light so as to facilitate an illumination of said contour with a predefined intensity pattern, said light being reflected in a corresponding intensity pattern indicative of said three dimensional contour on said object;
   second directing means on said housing means in the path of said reflected light from said contour for directing said reflected light to a desired location within said housing means;
   light sensing means located at said desired location for converting said intensity pattern of reflected light into a corresponding pattern of electrical data;
   contour memory means, and means for storing a selected set of said electrical data in said contour memory means;
   machining means for machining a workpiece in accordance with a set of electrical data sequentially presented thereto; and
   sequencing means for sequentially presenting said selected set of said electrical data to said machining means to cause a machining of said workpiece to a shape corresponding to said contour to enable the shaped workpiece to be fittingly placed onto said contour.

8. The apparatus according to claim 7, wherein said housing means is elongate and at least one end of said housing means is adapted to be received in the mouth of a human; and
   wherein said light from said light source means is emitted from said one end of said housing and said reflected light enters said one end of said housing.

9. The apparatus according to claim 8, wherein said second directing means includes lens means, wherein said light source means is located between said optical plate means and said lens means and is on a side of said lens means remote from said light sensing means.

10. The apparatus according to claim 9, wherein said housing means includes a mirror intermediate said lens means and said optical plate means as well as intermediate said light source means and said optical plate means, said mirror being oriented in the paths of said light emitted from said light source means and said reflected light.

11. The apparatus according to claim 7, wherein aid first directing means causes said predetermined intensity pattern to travel toward said contour in a first direction and to be reflected toward said second directing means in a second direction which is oriented at an angle to said first direction; wherein said predetermined intensity pattern includes alternating bright and dark regions uniformly spaced in a third direction extending perpendicular to said first direction and parallel to a plane containing said first and second directions, said contour causing portions of said bright and dark regions to be spatially shifted in said reflected pattern of light in a fourth direction extending perpendicular to said second direction and parallel to said plane containing said first and second directions, the width of each said dark region between adjacent said bright regions of said predetermined intensity pattern being greater than the difference between the maximum and minimum amounts of spatial shift caused by respective points on said contour which are spaced the maximum possible distance from each other in said second direction; and wherein said light sensing means includes means for measuring the average light intensity in each of a plurality of predetermined and stationary window regions which are uniformly spaced from each other in said fourth direction and which each have a predetermined width in said fourth direction, the intensity measured in each said window region being proportional to the actual physical position in said second direction of a corresponding portion of said contour.

12. The apparatus according to claim 7, including an aperture member disposed in the path of said light from said light source and having spaced first and second holes therethrough, said first directing means causing said light from said light source to pass through said first hole and said second directing means causing said light reflected from said contour on said object to pass through said second hole.

13. The apparatus according to claim 12, wherein said optical plate means is located between said light source and said aperture member.

14. The apparatus according to claim 13, wherein said light sensing means includes a sensor having a plurality of sensor elements arranged in a plurality of parallel rows, wherein said optical plate means includes a translucent plate having a plurality of opaque, spaced, parallel rulings thereon, and wherein light passing between two said rulings on said plate, after being reflected by said contour on said object, strikes said sensor in the region of a respective row of sensor elements thereon.

15. The apparatus according to claim 13, wherein said housing means has means defining a reference surface thereon in the region of an object being scanned and adjacent the path of light directed by said first directing means toward said contour on said object, a portion of said predetermined intensity pattern striking and being reflected by said reference surface and forming a portion of said reflected intensity pattern directed onto said light sensing means.

16. The apparatus according to claim 13, including an image-forming lens disposed adjacent said aperture member on a side thereof remote from said light source, wherein light traveling from said light source to said object passes through said image-forming lens and reflected light traveling from said object to said light sensing means travels through said image-forming lens, said image-forming lens being part of said first directing means and part of said second directing means.

17. The apparatus according to claim 16, wherein said first directing means includes condensing lens means disposed between said light source means and said aperture member and a first prism supported on said housing on a side of said image-forming lens means remote from said light source means for directing light from said image-forming lens means toward said object; and wherein said second directing means includes said first prism being adapted to direct light reflected from said object toward said aperture member, and includes a second prism which is located on a side of said aperture member remote from said first prism and directs light passing through said second hole in said aperture member toward said light sensing means.

18. An apparatus for facilitating the fabrication of a workpiece to be placed onto a light reflective object having a three-dimensional contour thereon to which said workpiece is to be conformed, comprising:

housing means;

light source means on said housing means and first directing means for directing the light from said light source means toward said contour;

optical plate means on said housing means interposed in the path of said light from said light source means for controlling the magnitude of said light so as to facilitate an illumination of said contour with a predefined intensity pattern, said light being reflected in a corresponding intensity pattern indicative of said three-dimensional contour on said object;

second directing means on said housing means in the path of said reflected light from said contour for directing said reflected light to a desired location within said housing means;

light sensing means located at said desired location for converting said intensity pattern of reflected light into a corresponding pattern of electrical data;

contour memory means, and means for storing a selected set of said electrical data in said contour memory means;

machining means for machining a workpiece in accordance with a set of electrical data sequentially presented thereto;

sequencing means for sequentially presenting said selected set of said electrical data to said machining means to cause a machining of said workpiece to a shape corresponding to said contour to enable the shaped workpiece to be fittingly placed onto said contour;

an aperture member disposed in the path of said light from said light source and having spaced first and second holes therethrough, said first directing means causing said light from said light source to pass through said first hole and said second directing means causing said light reflected from said contour on said object to pass through said second hole; and means for producing a second predetermined intensity pattern of light and means for causing a selected one of said first-mentioned and second intensity patterns to be directed onto said contour on said object;

wherein said means for storing data in said contour memory means includes processing means for accepting from said light sensing means a first set of electrical data corresponding to said first-mentioned intensity pattern and a second set of said electrical data corresponding to said second intensity pattern and for calculating a third set of electrical data from said first and second sets of data, said third set of electrical data being said selected set stored in said contour memory means.

19. A method for facilitating the fabrication of a workpiece to be placed onto a light reflective object having a three-dimensional contour thereon to which said workpiece is to be conformed, comprising the steps of:

noncontact topographic scanning of said contour on said object, including the step of directing a predetermined intensity pattern of light onto said contour so that a corresponding intensity pattern of light will be reflected therefrom, the varying intensity pattern of said reflected light being a measure of said three-dimensional contour on said object;

directing said pattern of said reflected light from said object onto a light sensing means;

converting said pattern of light on said light sensing means into a corresponding pattern of electrical data;

selecting a set of said electrical data;

storing said set of said electrical data;

directing a second predetermined intensity pattern of light onto said contour and directing the intensity pattern of light reflected from said object onto said light sensing means;

converting the pattern of light on said light sensing means into a corresponding pattern of electrical data and selecting therefrom a second set of electrical data;

calculating a third set of electrical data from said first-mentioned and second sets of electrical data;

storing said third set of electrical data in place of said first-mentioned set of electrical data;

mounting said workpiece onto a machining means which is responsive to electrical data sequentially presented thereto;

sequentially presenting said stored set of electrical data to said machining means; and machining said workpiece into a three-dimensional shape in accordance with said stored set of data.

20. An apparatus for faciitating the fabrication of a workpiece to be placed onto a light reflective object having a three-dimensional contour thereon to which said workpiece is to be conformed, comprising:

housing means;

light source means on said housing means and first directing means for directing the light from said light source means toward said contour;

optical plate means on said housing means interposed in the path of said light from said light source means for controlling the magnitude of said light so as to facilitate an illumination of said contour with a predefined intensity pattern, said light being reflected in a corresponding intensity pattern indicative of said three-dimensional contour on said object;

second directing means on said housing means in the path of said reflected light from said contour for directing said reflected light to a desired location within said housing means;

light sensing means located at said desired location for converting said intensity pattern of reflected light into a corresponding pattern of electrical data;

contour memory means, and means for storing a selected set of said electrical data in said contour memory means;

machining means for machining a workpiece in accordance with a set of electrical data sequentially presented thereto;

sequencing means for sequentially presenting said selected set of said electrical data to said machining means to cause a machining of said workpiece to a shape corresponding to said contour to enable the shaped workpiece to be fittingly placed onto said contour;

an aperture member disposed in the path of said light from said light source and having spaced first and second holes therethrough, said first directing means causing said light from said light source to pass through said first hole and said second directing means causing said light reflected from said contour on said object to pass through said second hole, said optical plate means being located between said light source and said aperture member; and means supporting said optical plate means for movement between first and second positions in a direction generally perpendicular to the direction of travel of light therethrough;

wherein said means for storing data in said contour memory means includes means for selectively effecting movement of said optical plate means to one of said first and second positions; and wherein said means for storing data in said contour memory means includes processing means for accepting first and second sets of electrical data produced by said light sensing means when said optical plate means is respectively in said first and second positions, and for calculating a third set of electrical data from said first and second sets, said third set of electrical data being said selected data set which is stored in said contour memory means and presented by said sequencing means to said machining means.

21. An apparatus for facilitating the fabrication of a workpiece to be placed onto a light reflective object having a three-dimensional contour thereon to which said workpiece is to be conformed, comprising:

means for noncontact topographic scanning of said contour on said object, including means for directing a first predetermined intensity pattern of light onto said contour so that a corresponding intensity pattern of light will be reflected therefrom, the varying intensity pattern of said reflected light being a measure of said three-dimensional contour on said object;

directing means for directing said pattern of said reflected light from said object onto light sensing means;

conversion means for converting said pattern of light on said light sensing means into a corresponding pattern of electrical data;

selection means for selecting a first set of said electrical data;

means for storing said first set of said electrical data;

means for directing a second predetermined intensity pattern of light onto said contour, said directing means directing the intensity pattern of light reflected from said object onto said light sensing means, said conversion means converting the pattern of light on said light sensing means into a corresponding pattern of electrical data, and said selection means selecting therefrom a second set of electrical data;

means for calculating a third set of electrical data from said first and second sets of electrical data;

means for storing said third set of electrical data;

machining means for machining the workpiece in response to electrical data sequentially presented thereto; and means for sequentially presenting said stored third set of electrical data to said machining means.

* * * * *

UNITED STATES PATENT AND TRADEMARK OFFICE
CERTIFICATE OF CORRECTION

PATENT NO. : 4 575 805
DATED : March 11, 1986
INVENTOR(S) : Werner H. Moermann and Marco Brandestini It is certified that error appears in the above-identified patent and that said Letters Patent is hereby corrected as shown below:

Column 15, line 1; change "aid" to ---said---.

Signed and Sealed this

Twenty-ninth Day of July 1986

[SEAL]

Attest:

DONALD J. QUIGG

Attesting Officer     Commissioner of Patents and Trademarks